US00PP12299P2

(12) United States Plant Patent
Jepsen

(10) Patent No.: US PP12,299 P2
(45) Date of Patent: Dec. 25, 2001

(54) KALANCHOE PLANT NAMED 'YELLOW AFRICAN'

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 3 days.

(21) Appl. No.: 09/822,009

(22) Filed: Mar. 31, 2001

(51) Int. Cl.[7] ..... A01H 5/00

(52) U.S. Cl. ..... Plt./338
(58) Field of Search ..... Plt./338, 335

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Kalanchoe plant named 'Yellow African', characterized by its numerous and large golden yellow-colored flowers; upright and vigorous plant habit; dark green dissected leaves; and excellent postproduction longevity.

2 Drawing Sheets

BACKGROUND OF THE INVENTION

The present invention relates to a new and distinct cultivar of Kalanchoe plant, botanically known as *Kalanchoe blossfeldiana*×*Kalanchoe laciniata*, and hereinafter referred to by the name 'Yellow African'.

The new Kalanchoe is a product of a planned breeding program conducted by the Inventor in Hinnerup, Denmark. The objective of the breeding program was to create new interspecific Kalanchoe cultivars with interesting flower colors and good postproduction longevity.

The new Kalanchoe originated from a cross made by the Inventor of the *Kalanchoe blossfeldiana* culivar Nadia, not patented, as the female, or seed, parent with an unidentified *Kalanchoe laciniata* seedling selection as the male, or pollen, parent. The cultivar Yellow African was discovered and selected by the Inventor as a flowering plant within the progeny of the stated cross in a controlled environment in Hinnerup, Denmark.

Asexual reproduction of the new Kalanchoe by terminal cuttings taken at Hinnerup, Denmark, by the Inventor, has shown that the unique features of this new Kalanchoe are stable and reproduced true to type in successive generations.

BRIEF SUMMARY OF THE INVENTION

The cultivar Yellow African has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yellow African'. These characteristics in combination distinguish 'Yellow African' as a new and distinct cutlivar:

1. Numerous and large golden yellow-colored flowers.
2. Upright and vigorous plant habit.
3. Dark green dissected leaves.
4. Excellent postproduction longevity.

Plants of the new Kalanchoe differ primarily from plants of the parents in flower color, leaf size, and leaf type. In addition, plants of the new Kalanchoe have much better longevity than plants of the male parent.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type. Colors in the photographs may differ slightly from the color values cited in the detailed botanical description which accurately describe the colors of the new Kalanchoe. The photographs were taken under diffuse natural light conditions on an overcast day with electronic flash at approximately noon in Hinnerup, Denmark.

The photograph on the first sheet comprises a side perspective view of a typical potted plant of 'Yellow African'.

The photograph at the top of the second sheet comprises a top perspective view of a typical potted plant of 'Yellow African' showing the flowers and foliage.

The photograph at the bottom of the second sheet is a close-up view of the following: side and top perspective views of a typical flowering cyme and top perspective views of immature and fully expanded leaves of 'Yellow African'.

DETAILED BOTANICAL DESCRIPTION

In the following description, color references are made to The Royal Horticultural Society Colour Chart except where general terms of ordinary dictionary significance are used. Unpinched plants used in the photographs and for the following observations and measurements were grown in Hinnerup, Denmark, under commercial practice in a glass-covered greenhouse for about 12 weeks after the start of short day/long night photoperiodic treatment with average temperatures of 20° C.

Botanical classification: *Kalanchoe blossfieldiana*× *Kalanchoe laciniata* cultivar Yellow African.

Parentage:

*Female, or seed, parent.*—*Kalanchoe blossfeldiana* cultivar Nadia, not patented.

*Male, or pollen, parent.*—Unidentified *Kalanchoe laciniata* proprietary seedling selection, not patented.

Propagation:

*Type cutting.*—Terminal cuttings.

*Time to initiate roots.*—About 14 days.

*Root description.*—Numerous, fine, fibrous, and well-branched.

Plant description:

*Form.*—Upright, tall and vigorous plant habit with numerous compound cymes; freely flowering. Actual plant shape will depend on whether or not plants are pinched (apical terminals removed). Finished plant size is appropriate for one plant per 13-cm container.

*Branching habit.*—Freely branching. Pinching (removal of terminal apex) enhances lateral branch development.

*Plant height at flowering.*—About 38 cm.

*Plant diameter at flowering.*—About 35 cm.

*Folige description.*—Leaves simple, opposite, generally symmetrical. Size: Mature foliage size is reduced after floral induction. Vegetative plants: Length: About 22 cm. Width: About 18 cm. Reproductive plants: Length: About 10 cm. Width: About 8 cm. Shape: Tri-parted, deeply dissected. Apex: Obtuse. Base: Cuneate to truncate. Margin: Parted. Aspect: Slightly concave. Texture: Leathery, glabrous, succulent. Color: Young foliage, upper surface: 137B, glossy. Young foliage, lower surface: 137C. Mature foliage, upper surface: 147A, glossy. Mature foliage, lower surface: 137C.

Flower description:

*Flower type and habit.*—Single flowers arranged in compound dichasial cymes that arise from leaf axils. Upright flowering stems. Freely flowering. Flowers persistent.

*Natural flowering season.*—Late autumn/winter/early spring; flower initiation and development can be induced under short day/long night conditions.

*Time to flower.*—In the summer with 20° C. growing temperatures, about 10 weeks of short day/long night conditions are required to produce flowering plants. During the winter with supplemental lighting and 20° C. growing temperatures, about 12 weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About 1.5 weeks after the first flower has opened, 50% of the remaining flowers are open.

*Post-production longevity.*—Plants of the new Kalanchoe maintain good leaf and flower substance for at least five weeks under interior environmental conditions.

*Flower diameter.*—About 2.5 cm.

*Quantity.*—Very freely flowering, at least 250 flowers per plant.

*Flower buds.*—Shape: Narrowly oblong. Length: About 1.6 cm. Width: About 3 mm. Color: 11B.

*Petals.*—Quantity: Four fused at base. Length: About 1.2 cm. Shape: Round obovate. Apex: Cuspidate. Margin: Entire. Texture: Glabrous, smooth and satiny. Color: Upper surface: 14B, becoming 21B with subsequent development. Lower surface: 10C.

*Reproductive organs.*—Stamens: Stamen number: Eight. Anther shape: Slightly oblong. Filament color: Green. Pollen color: Yellow. Pistils: Pistil number: Four. Style color: Green. Stigma shape: Round. Ovaries: Superior and four-celled. Ovary size: About 7 mm by 3 mm. Ovary color: Light green.

*Seed.*—Seed production has not been observed.

Disease resistance: Resistance to known Kalanchoe diseases has not been observed on plants of the new Kalanchoe grown under commercial greenhouse conditions.

It is claimed:

1. A new and distinct cultivar of Kalanchoe plant named 'Yellow African', as illustrated and described.

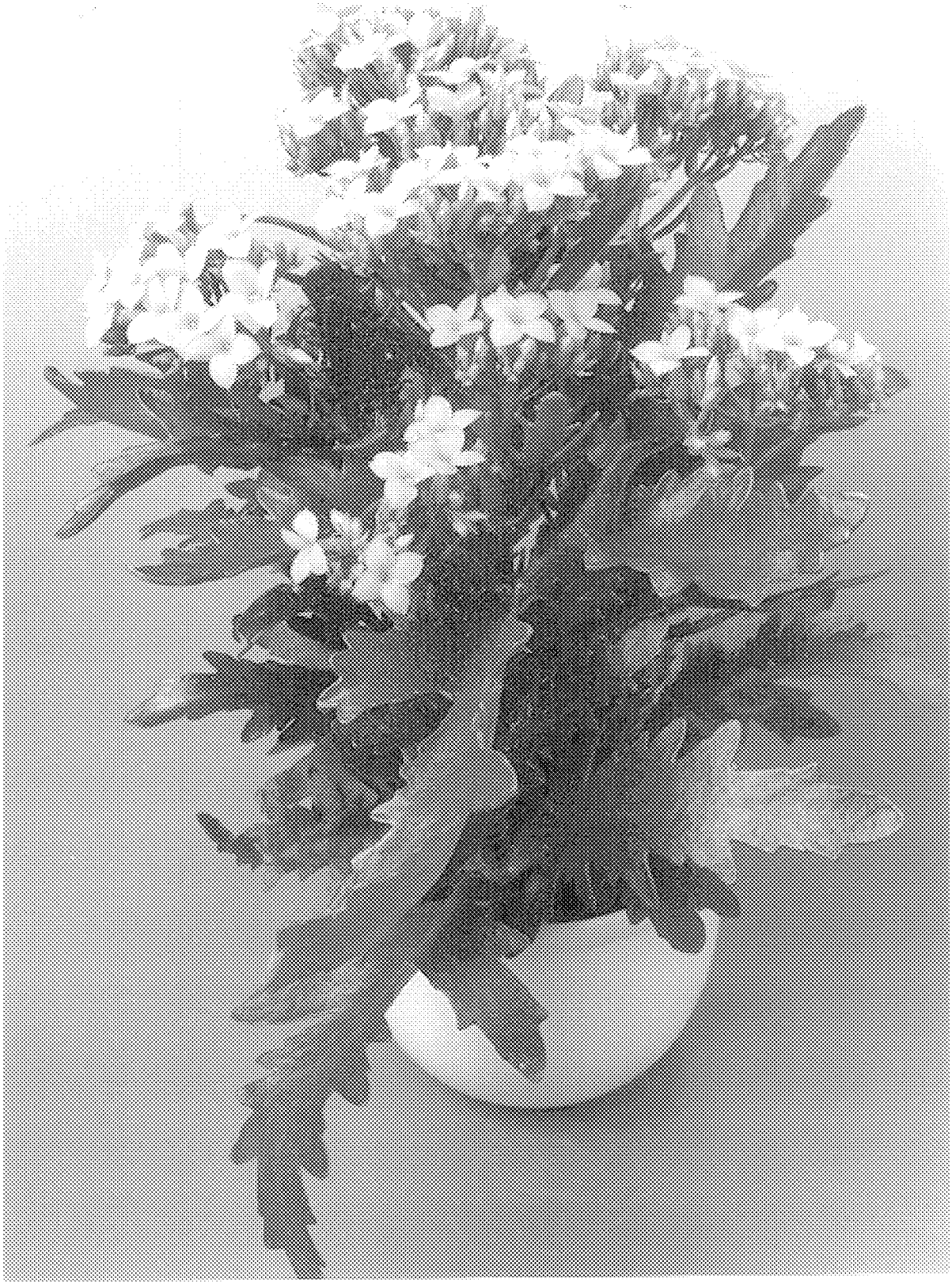

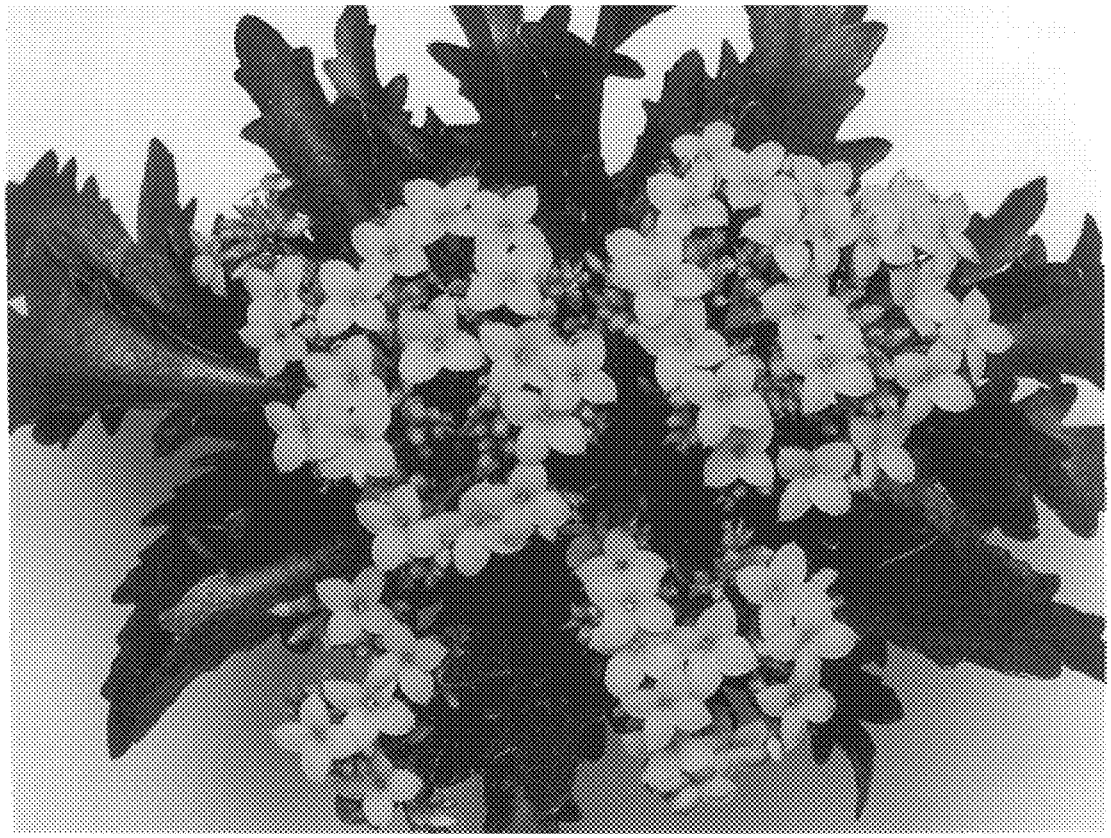
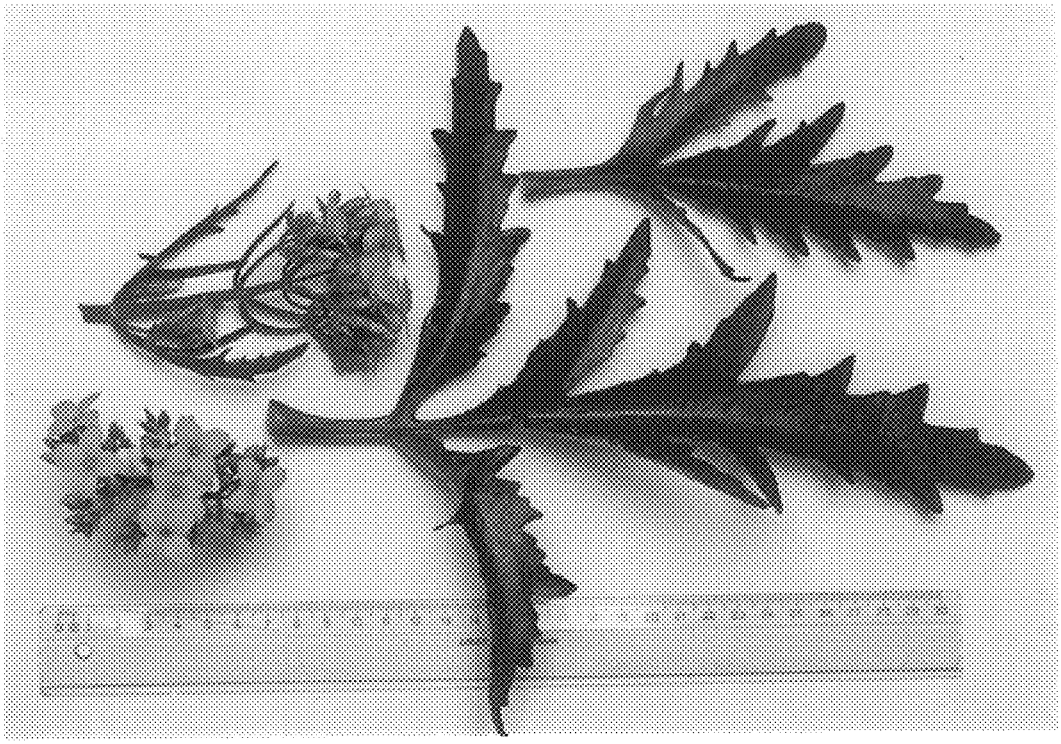

* * * * *